(12) United States Patent
Birngruber et al.

(10) Patent No.: US 9,656,018 B2
(45) Date of Patent: May 23, 2017

(54) CATHETER HAVING A HEALING DUMMY

(75) Inventors: Thomas Birngruber, Graz (AT);
Thomas Kroath, Graz (AT)

(73) Assignee: JOANNEUM RESEARCH FORSCHUNGSGESELLSCH, Graz (AT)

( * ) Notice: Subject to any disclaimer, the term of this patent is extended or adjusted under 35 U.S.C. 154(b) by 783 days.

(21) Appl. No.: 14/118,128

(22) PCT Filed: May 16, 2012

(86) PCT No.: PCT/EP2012/059192
§ 371 (c)(1),
(2), (4) Date: Jan. 17, 2014

(87) PCT Pub. No.: WO2012/156478
PCT Pub. Date: Nov. 22, 2012

(65) Prior Publication Data
US 2014/0163458 A1    Jun. 12, 2014

(30) Foreign Application Priority Data
May 17, 2011 (EP) .................. 11166411

(51) Int. Cl.
*A61M 1/00* (2006.01)
*A61M 3/00* (2006.01)
(Continued)

(52) U.S. Cl.
CPC ..... *A61M 5/14276* (2013.01); *A61B 5/14507* (2013.01); *A61B 5/14525* (2013.01);
(Continued)

(58) Field of Classification Search
CPC ............ A61B 5/14507; A61B 5/14525; A61B 5/14532; A61B 17/1204; A61M 1/0084;
(Continued)

(56) References Cited

U.S. PATENT DOCUMENTS 5,097,834 A    3/1992  Skrabal
5,372,582 A *  12/1994 Skrabal ............ A61M 25/0026
                                                    604/164.11
(Continued)

FOREIGN PATENT DOCUMENTS

EP    2258416 A1    12/2010
WO    02056937 A2    7/2002
(Continued)

*Primary Examiner* — Jason Flick
(74) *Attorney, Agent, or Firm* — Robert A. Blaha; Smith Tempel Blaha LL

(57) ABSTRACT

A catheter for implantation into tissue, the catheter comprising a tubing having a lumen and defining an outer boundary between the catheter and the tissue when the catheter is implanted in the tissue, a healing dummy being insertable in the lumen with clearance so as to prevent tissue ingrowth from the tissue into the lumen when the healing dummy is within the lumen, wherein the healing dummy is removable from the lumen by pulling the healing dummy relative to the tubing out of the lumen, and a perfusion insert being insertable in the lumen when the healing dummy is removed from the lumen, being configured for supplying a perfusion fluid to the tissue so as to initiate interaction between the perfusion fluid and tissue, and being configured for collecting perfusion fluid after interaction with tissue.

19 Claims, 3 Drawing Sheets

(51) Int. Cl.
*A61M 5/142* (2006.01)
*A61B 5/145* (2006.01)
*A61M 25/00* (2006.01)
*A61M 39/02* (2006.01)

(52) U.S. Cl.
CPC ....... *A61B 5/14532* (2013.01); *A61M 1/0084* (2013.01); *A61M 25/0017* (2013.01); *A61M 39/02* (2013.01); *A61M 2025/0018* (2013.01); *A61M 2039/025* (2013.01); *A61M 2039/0273* (2013.01)

(58) Field of Classification Search
CPC ...... A61M 2025/0018; A61M 25/0017; A61M 39/02; A61M 5/14276; A61M 2039/025; A61M 2039/0273
USPC .......................................................... 604/28
See application file for complete search history.

(56) References Cited

U.S. PATENT DOCUMENTS

| | | |
|---|---|---|
| 5,441,481 A | 8/1995 | Mishra et al. |
| 2003/0014008 A1* | 1/2003 | Jacques .............. A61M 25/0023 604/96.01 |
| 2004/0138562 A1* | 7/2004 | Makower .......... A61M 25/0084 600/439 |
| 2004/0153028 A1* | 8/2004 | Diermann ............ A61B 5/1405 604/33 |
| 2006/0235349 A1 | 10/2006 | Osborn et al. |
| 2008/0103456 A1* | 5/2008 | Johnson ................ A61B 5/6864 604/264 |
| 2008/0119789 A1* | 5/2008 | Kaemmerer ...... A61M 39/0208 604/116 |
| 2008/0234563 A1 | 9/2008 | Regittnig |
| 2011/0084019 A1* | 4/2011 | Shiratori ................. A61L 27/34 210/506 |
| 2012/0071841 A1* | 3/2012 | Bengtson .............. A61M 1/008 604/313 |

FOREIGN PATENT DOCUMENTS

| | | | |
|---|---|---|---|
| WO | 2004096314 A2 | 11/2004 | |
| WO | 2007138590 A2 | 12/2007 | |
| WO | 2009158007 A2 | 12/2009 | |
| WO | WO 2009158007 A2 * | 12/2009 | .......... A61K 31/485 |
| WO | 2010031515 A1 | 3/2010 | |

* cited by examiner

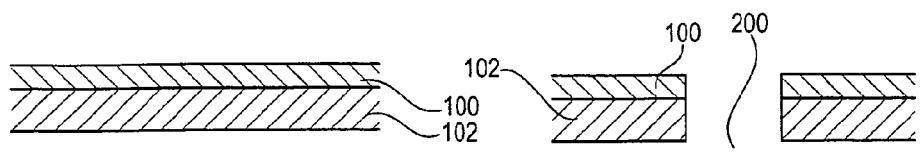
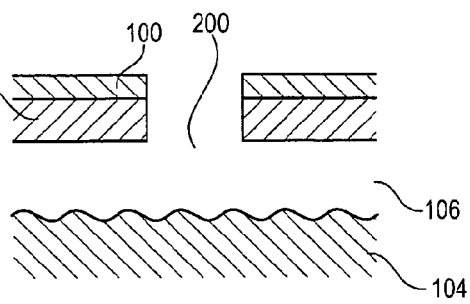
Fig. 1  Fig. 2
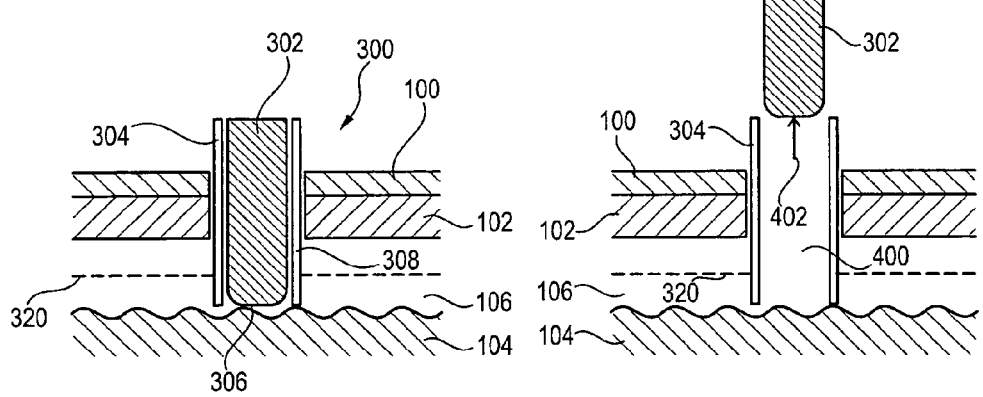
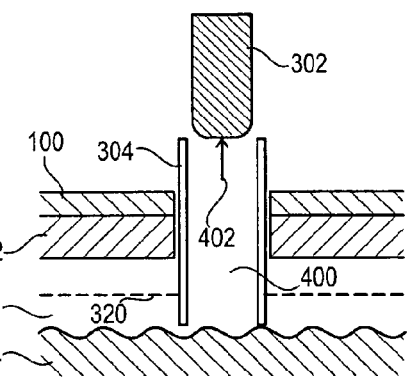
Fig. 3  Fig. 4
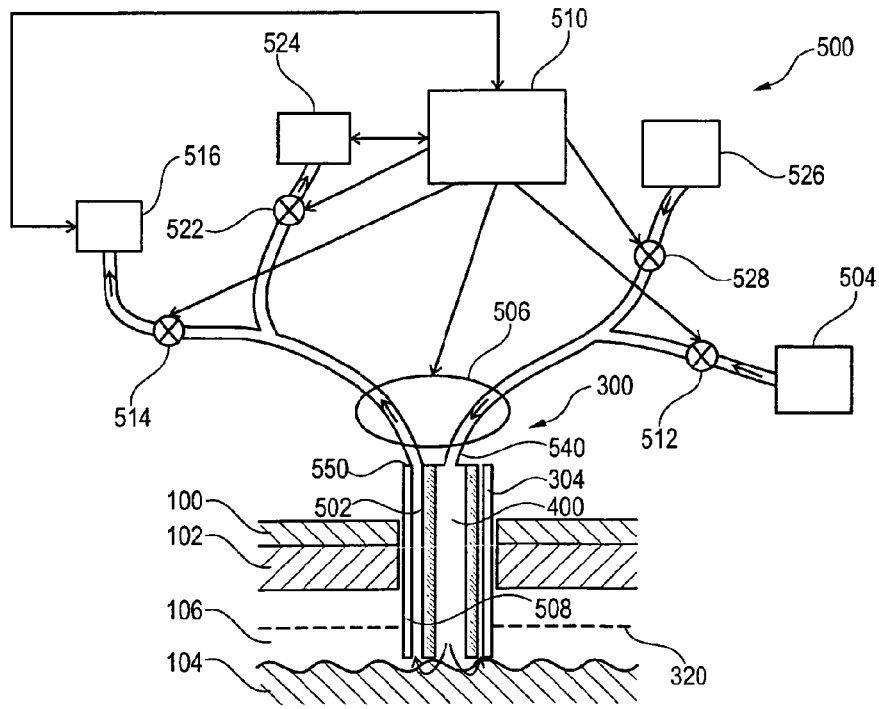
Fig. 5

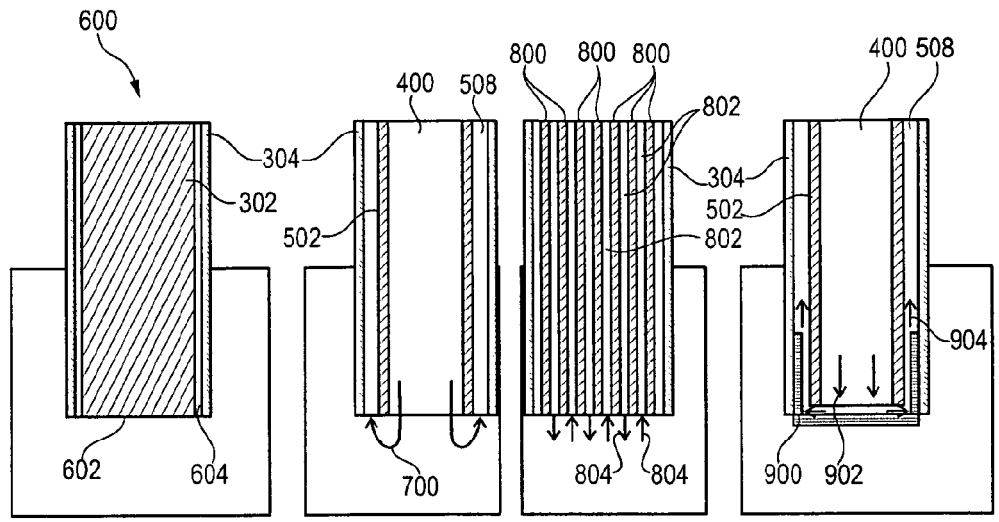
Fig. 6   Fig. 7   Fig. 8   Fig. 9
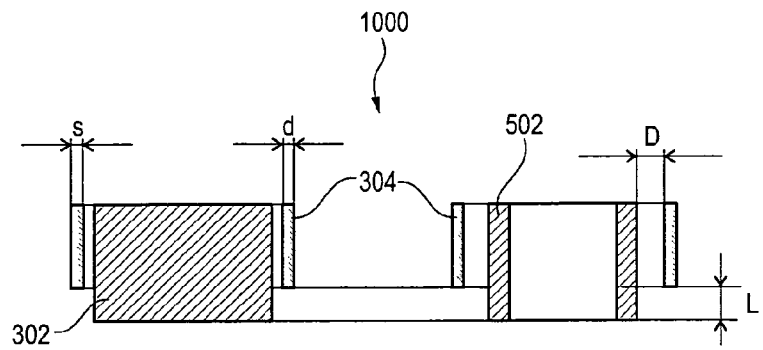
Fig. 10
| Substance | Amount |
|---|---|
| NaCl | 123 mmol/l |
| MgCl | 0,4 mmol/l |
| CaCl$_2$ | 0,7 mmol/l |
| KCl | 4,3 mmol/l |
| NaH$_2$PO$_4$ | 1,3 mmol/l |
| Na$_2$HPO$_4$ | 21 mmol/l |
| Glucose | 4 mmol/l |
Fig. 11
| Substance | Amount |
|---|---|
| Na | 130 ± 10 mmol/l |
| K | 4.3 ± 0.5 mmol/l |
| Ca | 0.72 ± 0.1 mmol/l |
| Mg | 0.4 ± 0.08 mmol/l |
| Cl | 135 ± 10 mmol/l |
| Glucose | 3 ± 1 mmol/l |
| pH | 7,4 ± 0,2 |
Fig. 12

CATHETER HAVING A HEALING DUMMY

This application claims the benefit of the filing date of European Patent Application 11166411.6 filed May 17, 2011, the disclosure of which is hereby incorporated herein by reference.

TECHNICAL FIELD

The invention relates to a catheter for implantation into a tissue.

Moreover, the invention relates to a medical system.

Beyond this, the invention relates to a method of implanting a catheter into a brain.

BACKGROUND

In "open-flow microperfusion" (OFM), in order to capture the alterations or levels of biochemical entities at tissue level in vivo for instance blood glucose levels subcutaneously, a needle-like catheter may be inserted into tissue, for instance in adipose tissue, muscle tissue, or skin. Linear catheters with a single lumen and an exchange area can be used to establish flow-through path for perfusion fluid. Using a double-lumen catheter, a perfusion fluid is continuously infused through the inner lumen and withdrawn through the annular space between the inner cannula and the outer catheter tubing. Because of partial equilibration between the interstitial fluid and the perfusate, the perfusate is enriched by surrounding substances (or solutes, entities, molecules), such that the substances can be detected in the outflow. For instance, a glucose sensor outside the body can capture glucose from the aspirated fluid. The fluid in the outflow (sample, aspirated fluid) is not a dialysate resulting from a membrane process, but to keep the analogy between microdialysis and microperfusion the term "dialysate" herein may also mean microperfusion outflows fluids.

However, implantation of a cerebral catheter into a brain involves injuries of the brain. Particularly, cerebral OFM is rendered difficult when using conventional approaches.

When implanting a cerebral catheter, the so-called blood-brain barrier can be disturbed or even disabled by the injury of the brain being caused by the implantation. The intact blood-brain barrier provides for a separation of circulating blood and cerebral extracellular fluid in the central nervous system. Endothelial cells restrict the diffusion of microscopic objects (for instance bacteria) and large or hydrophilic molecules into the central nervous system, while allowing the diffusion of small hydrophobic molecules ($O_2$, $CO_2$, neuroactive drugs,).

As long as the blood-brain barrier remains disturbed or even disabled by the injury, no meaningful OFM or microdialysis measurement of transport over blood-brain barrier is possible. On the other hand, maintaining the implanted catheter in the brain until the blood-brain barrier has recovered is not possible as well, since this procedure may take several days so that cerebral tissue may grow into the catheter during this time. This renders cerebral catheter technology very difficult.

Although cerebral catheters are specifically delicate, different types of catheters suffer from problems arising from the risk of injury during implantation or removal.

WO 2002/056937 discloses a system for delivering substances or apparatus to an extravascular target site within the body of a human or veterinary patient, said system comprising a vessel wall penetrating catheter that comprises a catheter body that is insertable into the vasculature of the patient and a vessel wall penetrating member having a lumen extending longitudinally therethrough, said penetrating member being passable from the catheter body and through the wall of a blood vessel in which the catheter body is positioned, and a delivery catheter having a lumen extending longitudinally therethrough, said delivery catheter being advanceable through the lumen of the vessel wall penetrating member to an extravascular target site, said vessel wall penetrating member being retractable into the catheter body of the vessel wall penetrating catheter and the vessel wall penetrating catheter being removable from the patient's body such that the delivery catheter remains indwelling with the distal end of the delivery catheter located at the extravascular target site.

WO 2004/096314 discloses a catheter assembly for intracranial treatment of a patient, wherein the assembly comprises an outer catheter and an inner catheter. The outer catheter includes a proximal opening, at least one aperture, a lumen connecting the opening and the aperture, and at least one element. The inner catheter is adapted to be received within the lumen and includes a passageway and at least one port for transferring fluids between the inner catheter and a tissue region within the patient's brain. The assembly facilitates regular accurate placement of the drug delivery catheter at the tissue region without additional extended contact with the brain during insertion.

WO 2007/138590 discloses an implantable pump for pumping a drug in a patient's body. The pump includes a drug delivery chamber configured to be filled with the drug and a drug delivery catheter having a catheter lumen and a distal end, the drug delivery catheter in fluid communication with the drug delivery chamber and configured to deliver the drug to a delivery site. It also includes a pushing element coupled to the distal end of the catheter, and configured to push away from the catheter lumen fibrotic matter that has developed in response to the drug delivery catheter.

US 2006/235349 discloses cerebrospinal fluid shunts (implantable devices for diversion of excess fluid from the brain to other body cavities) used to treat hydrocephalus often malfunction. A common etiology of shunt malfunction is obstruction of the distal catheter tip by accumulating particulate matter such as fat or proteinaceous debris. The proposed implantable device maintains the patency of the cerebrospinal fluid shunt with mechanical energy which serves to "scrub" the catheter lumen of particulate debris. The device accomplishes this by housing a source of mechanical energy which is coupled to the external aspect of the catheter, itself traversing through a bore in the device. The energy source secondarily induces a waveform in the cerebrospinal fluid flowing through the catheter. The fluid waveform exerts shearing forces on the catheter wall and serves to disrupt the formation and accumulation of debris that potentially could occlude the shunt catheter, thereby maintaining patency of the shunt.

It is however a shortcoming that conventional approaches do not allow to safely prevent ingrowth of tissue into a catheter which may cause problems when the catheter or parts thereof are maneuvered within a physiological body.

SUMMARY

There may be a need for a catheter for implantation into tissue which is implantable so that the execution of OFM, microdialysis, or a related technology is possible.

According to exemplary embodiments, a catheter for implantation into tissue, a medical system, and a method of implanting a catheter into tissue according to the independent claims are provided.

According to an exemplary embodiment of the invention, a catheter (particularly a cerebral catheter) for implantation into tissue (particularly a brain) is provided, the catheter comprising a (particularly flexible) tubing having a lumen and defining at least partially an outer boundary between the catheter and the tissue when the catheter is implanted in the tissue, a healing dummy being insertable in the lumen with clearance so as to prevent tissue growth from the tissue into the lumen (also denoted as ingrowth from the tissue into the lumen) when the healing dummy is within the lumen, wherein the healing dummy is removable from the lumen by pulling the healing dummy relative to the tubing out of the lumen, and a perfusion insert being insertable in the lumen when the healing dummy is removed from the lumen, being configured for supplying a perfusion fluid to the tissue so as to initiate interaction between the perfusion fluid and the tissue, and being configured for collecting perfusion fluid after interaction with the tissue.

According to another exemplary embodiment of the invention, a medical system is provided which comprises a catheter having the above mentioned features and being configured to be inserted into tissue of a physiological subject, and a pump being in fluid communication with the catheter for conducting a perfusion fluid towards the catheter and for conducting a sample fluid resulting from an interaction of the perfusion fluid with the tissue away from the catheter.

According to still another exemplary embodiment of the invention, a method of implanting a catheter (particularly a cerebral catheter) into tissue (particularly brain) is provided, wherein the method comprises implanting the catheter into the tissue so that a (particularly flexible) tubing having a lumen defines at least partially an outer boundary between the catheter and the tissue, inserting a healing dummy in the lumen with clearance so as to prevent tissue ingrowth from the tissue into the lumen when the healing dummy is within the lumen and maintaining the healing dummy in the lumen for a predefined healing time (for instance 10 hours to 20 days), after expiry of the healing time, removing the healing dummy from the lumen by pulling the healing dummy relative to the tubing out of the lumen, after the removing, inserting a perfusion insert in the lumen for supplying a perfusion fluid to the tissue so as to initiate interaction between the perfusion fluid and the tissue, and collecting perfusion fluid after the interaction with the tissue.

In the context of this application, the term "catheter" may particularly denote a tube (or any differently shaped geometrical structure) that can be inserted into a body, wherein upon inserting the catheter into the body, the catheter may generate itself a cavity in which the catheter is accommodated. A catheter may also be inserted into an existing body cavity. A catheter may comprise one or more flexible or rigid tubings. Its diameter may vary particularly between 0.1 mm and 10 mm. A catheter may have an exchange surface (such as a permeable membrane or one or more small gaps between adjacent tubes) via which substances can be exchanged between an interior and an exterior of the catheter. Cerebral catheterization is a technique where a catheter is navigated to a brain.

The term "tubing" may particularly denote a tubular or hollow cylindrical structure enclosing a lumen (i.e. a fluidic conduit along which a fluid is conductable) and being made of a bioinert material sufficiently smooth to keep injuries during the implantation as small as possible.

The term "healing dummy" may particularly denote a body being made of a bioinert material and being temporarily insertable into an open lumen of the tubing so as to basically close the lumen during a time interval which the tissue requires for healing an injury which may be caused by the implantation of the catheter. Hence, tubing and healing dummy should be designed to correspond to one another regarding size, shape and material (since tubing and healing dummy shall function as a tribological pair being slidable relative to one another with low friction).

The term "clearance" may particularly denote a distance between tubing and healing body being as small as possible to avoid a large gap but at the same time sufficiently large to prevent the appearance of touching or even clamping between healing dummy and tubing. The clearance is to be selected so that insertion of the healing dummy into the tubing and removal of the healing dummy from the tubing is not disturbed by friction forces between the tubing and the healing dummy to such an extent that particularly the removing actions causes anew injury of the tissue, for instance the brain. Functionally, the clearance shall be designed such that a frictionless insertion and removal of the healing dummy in and out of the flexible tubing is enabled, simultaneously preventing cell growth in a corresponding gap.

The term "tissue ingrowth" (also denoted as "tissue growth") may particularly denote the natural process of growth of tissue in the physiological subject. The gap between the tubing and the healing dummy should be made sufficiently small so as to prevent that such a process forms new organic material between the tubing and the healing dummy which material could cause anew injury when removing the healing dummy.

The term "perfusion insert" may particularly denote a component configured to be insertable into the tubing to substitute the healing dummy such that the tubing plus the perfusion insert together form a regular catheter allowing for a supply of a perfusion fluid to the tissue, particularly brain, for exchange with surrounding tissue including body fluids such as cerebrospinal fluid or any kind of brain tissue, and allowing for extracting or recovering a mixture of the perfusion fluid with the cerebrospinal fluid or brain tissue.

The term "perfusion fluid" may particularly denote a fluid (such as a buffer, water, a medication, etc.) which may be brought in interaction with body fluid/solid tissue via an exchange surface of the catheter so that a material transport from the body fluid/solid tissue to the perfusion fluid (or vice versa) may allow to analyze a component of the body fluid/solid tissue by analyzing the modified perfusate. The term "perfusion fluid" may denote the liquid entering a lumen of the catheter.

The term "sample fluid" or "dialysis fluid" or "dialysate" may denote the liquid resulting when perfusion fluid has interacted, particularly via a permeable membrane or via a small exchange gap, with tissue such as brain tissue.

The term "brain tissue" may particularly denote any physiological substance of the brain in a liquid and/or solid phase, including intra- and extracellular brain fluid, brain cells, and also an aggregate of cells and cell material forming a structural material of an organism or physiological subject.

The term "physiological subject" or biological subject may particularly denote any human being and any animal (any organism).

The term "healing time" may particularly denote a time interval required by the physiological subject to carry out healing processes so as to heal a potential injury resulting from the implantation process of the catheter. Particularly in a brain, such an implantation injury may cause disturbance or loss of the blood-brain barrier. In a human organism for instance, it may take several days (for instance 20 days) until such an injury is repaired and the blood-brain barrier is intact again.

According to an exemplary embodiment of the invention, a catheter system is provided which allows for a reliable determination of the physiological condition within a body part such as the brain of a physiological subject. For this purpose, a for example flexible tubing may be implanted into the body part, particularly the brain (for instance after having formed an access bore through the cranium). The process of forming the access to the body part, particularly the brain, and inserting the tubing into the access hole may cause injury of the body part, particularly the brain, which in case of the brain may even have the consequence that the blood-brain barrier is disturbed or deactivated. In this physiological state, a meaningful measurement of a physiological condition is not possible in many cases. Hence, a healing dummy is inserted into the flexible tubing so that tubing and healing dummy form a non-traumatic structure promoting the healing process and simultaneously inhibiting growth of tissue, particularly brain tissue, at an interface between tubing and healing dummy. Hence, the remaining gap between tubing and healing dummy required for a low friction insertion and removal of the healing dummy can be rendered so small that it does not allow tissue to grow in this gap. The flexibility of the tubing and the bioinert property of the healing dummy fitting to the tubing allow to securely prevent further injury of the body part, particularly the brain, after this implantation process, i.e. during a healing process. In other words, the healing dummy may serve as a placeholder for the perfusion insert until injuries of the body part, particularly the brain, due to the implantation process are healed. After an appropriate waiting time which depends on the degree of injury and the physiological subject, it can be reasonably expected that the blood-brain barrier has recovered or that other kind of injury disturbing a measurement process has healed to a sufficient degree. After such a time interval, the healing dummy may be smoothly retracted and therefore removed from the tubing and may be substituted by the perfusion insert. Therefore, the tubing remaining within the physiological subject during this substitution serves as an anti-traumatic anchor and prevents further injury to occur. In case of an implantation of a catheter in a brain, after the perfusion insert has been inserted into the flexible tubing, it is optionally possible to verify recovery of the blood-brain barrier by injecting a corresponding marker into the blood of the patient and measuring via the cerebral catheter whether this marker can be detected as well. After successful optional verification that the blood-brain barrier has recovered, an actual perfusion process may be initiated, for instance for measuring a physiological parameter for example by microdialysis or microperfusion.

According to an exemplary embodiment, a catheter (for instance a cerebral catheter) comprising a wound healing dummy is provided, particularly for cerebral OFM (open-flow microperfusion). More particularly, an invasive catheter is provided which allows the healing of the implantation trauma and prevents formation of a new trauma prior to and during the measurement of a physiological parameter.

In the following, further exemplary embodiments of the catheter will be explained. However, these embodiments also apply to the medical system and the method.

In an embodiment, the catheter may be configured so that, when the healing dummy is inserted in the lumen to prevent tissue ingrowth, the healing dummy and the tubing may be in flush (i.e. the healing dummy may be inserted in the tubing with aligned proximal end faces without protruding over the tubing and at the same time without (apart from a slight gap in view of the clearance) forming a recess in a front portion of the tubing, so that the healing dummy and the tubing together form a flat and planar structure at a common front face). Alternatively, the front surface of the healing dummy may protrude, along a direction along which the healing dummy or the perfusion insert is inserted into the tubing, over the open lumen of the tubing by a distance in a range between 0 and 0.5 mm. A flushing between front face of healing dummy and front face of tubing is highly preferred because this fully avoids anew injury of tissue after primary implantation of the catheter when operating the catheter to convert it between a healing dummy mode and a perfusion mode. However, a slight protrusion of the healing dummy over the tubing has turned out to be still a significant improvement, in terms of avoidance of anew injury, over a mode in which the healing dummy is retracted with regard to the tubing (thereby forming a cup-like recess).

More particularly, the healing dummy and the tubing may be configured so that, when the healing dummy is inserted in the lumen to prevent tissue from ingrowing into the lumen, the front or proximal surface of the healing dummy protrudes, along a direction along which the healing dummy or the perfusion insert is inserted into the tubing, over the open lumen of the tubing by a distance in a range between zero and 0.5 mm. By providing the healing dummy with a front face flushing with or only slightly protruding over the front opening of the tubing rather than providing openings at the lateral surface of the tubing has the advantage of safely preventing any undesired tissue ingrowth in such lateral wall openings. Such lateral wall openings could never be closed completely by a healing dummy being longitudinally movable (for instance reciprocatable) along the lumen of the tubing. However, by foreseeing a front opening in the front face of the tubing which can be closed by the flushing or marginally protruding healing dummy, such undesired lateral tissue ingrowth may be safely prevented. Furthermore, the provision of a front opening in the front face of the tubing which can be closed by the flushing or even slightly protruding healing dummy according to an embodiment of the invention has the advantage over one or more lateral openings in the side wall of the tubing that the exchange efficiency between the perfusion fluid and the tissue is significantly better. It is believed that this improvement is due to the basically 180° inversion of the fluid flow at the front face opening of the catheter. In contrast to this, lateral openings of conventional approaches involve smaller angles of fluid flow changes which cannot achieve these efficiencies of fluid exchange.

In a preferred embodiment, also the perfusion insert and the tubing are in flush (i.e. the perfusion insert may be inserted in the tubing with aligned proximal end faces without protruding over the tubing and at the same time without (apart from a slight gap in view of a clearance and/or a fluidic channel) forming a recess in a front portion of the tubing, so that the perfusion insert and the tubing together form a basically flat and planar structure at a common front face), or the perfusion insert protrudes along an insertion direction over the tubing by a distance in a range between 0 and 0.5 mm. More particularly, the perfusion insert and the tubing may be configured so that, when the perfusion insert is inserted in the lumen, the front surface of the perfusion insert protrudes, along a direction along which the healing dummy or the perfusion insert is inserted into the tubing, over the open lumen of the tubing by a distance in a range between zero and 0.5 mm. By providing the perfusion insert with a front face flushing with or slightly protruding over the front opening of the tubing rather than providing openings at the lateral surface of the tubing has the advantage of safely preventing any undesired tissue ingrowth in such lateral wall openings in a perfusion operation mode.

By providing both the healing dummy and the tubing as well as the perfusion insert and the tubing to flush thereby forming a for instance flat and/or planar front face being free or basically free of a protrusion, an anew injury of the tissue due to the maneuvering of healing dummy or perfusion insert may be safely avoided after the initial implantation of the catheter.

In an embodiment, the healing dummy is configured to basically completely fill the opening in the tubing so that basically no recess remains in the tubing when the healing dummy is inserted into the tubing. Particularly, the tubing may be free of lateral recesses which are located at such a lateral surface of the tubing that the healing dummy reciprocating in the lumen without being capable of entirely closing the lateral recesses.

Correspondingly, the perfusion insert may be configured to basically fill the opening in the tubing apart from one or more fluid channels formed by the perfusion insert itself and/or between the perfusion insert and the flexible tubing.

The following embodiments are predominantly described referring to a cerebral catheter for implantation into a brain. However, it should be emphasized that embodiments of the invention may also be used for other catheter applications, i.e. to be implanted in other body parts such as bones, skin, adipose tissue, muscle tissue, and/or cartilage tissue. Hence, all following embodiments also apply for other kinds of catheters as well.

In an embodiment, the healing dummy comprises a venting unit configured for venting a region between the healing dummy and the tissue upon pulling the healing dummy relative to the tubing out of the lumen. For instance, such a venting unit may be realized as one or more vent holes in the healing dummy. Such one or more vent holes should be sufficiently small to prevent tissue ingrowth, i.e. can for instance have a diameter of the same size as the clearance between the tubing and the healing dummy. Upon retracting the piston-like healing dummy with regard to the tubing, it may happen under undesired circumstances (for instance small gap to the tubing, undesired conical geometry of a closure) that an underpressure is generated at a boundary between brain tissue and healing dummy. This causes the danger of injuring the brain tissue. Hence, by providing a ventilation feature at the healing dummy supplying a gas such as air, nitrogen, helium to this boundary, an injury may be safely prevented. Hence, insertion and/or removal of the healing dummy may be performed without mechanical, hydraulic, pneumatic interference.

In an embodiment, the tubing is a flexible tubing. The flexibility may further reduce the risk of injuries during implantation, stay and removal of the catheter in the body. The term "flexible" may particularly denote a material property of the tubing, namely that the tubing can be reversibly deformed under the influence of an external force having an order of magnitude of several Newton. Thus, the flexibility may include an elastic behavior, i.e. a reversible squeezability in contrast to a plastic deformation.

In an embodiment, the healing dummy has an edgeless, particularly a rounded, surface facing the brain when being inserted in the flexible tubing. By providing the healing dummy from a rounded structure, the probability of undesired injuries in the time interval during which the healing dummy remains within the flexible tube may be further reduced. Particularly, the healing dummy may be free of any cutting edges or sharp tips.

In an embodiment, the healing dummy has a cylindrical shape and the flexible tubing has a hollow cylindrical shape. Particularly, the healing dummy may have a circular cylindrical shape and the flexible tubing may have a hollow circular cylindrical shape. This geometry allows to prevent injuries during the implantation process to a minimum.

In an embodiment, the healing dummy protrudes along an insertion direction (i.e. in a direction along which the healing dummy or the perfusion insert is inserted into the tubing) over the flexible tubing by a distance in a range between zero and about 0.5 mm. Hence, healing dummy and flexible tubing may be in flush, or the healing dummy may slightly protrude over the flexible tubing. Hence, a length of the flexible tubing along an insertion direction will not be larger and will be at the maximum about 0.5 mm shorter than a length of the healing dummy. Thus, any recess of the tubing-healing dummy arrangement which could serve as a place for growth of tissue can be prevented when the flexible tubing and the healing dummy either are flush with one another or if the healing dummy slightly protrudes over the flexible tube. Particularly, the healing dummy and the perfusion insert may have the same length along the insertion direction.

In an embodiment, the perfusion insert protrudes along an insertion direction over the flexible tubing by a distance in a range between zero and about 0.5 mm. Thus, it can be ensured that the arrangement of tubing and perfusion insert is prone to growth of tissue which could cause a further injury when removing the catheter and which could also disturb the interaction between the physiological substances in the brain and the perfusion fluid. It is also believed that this geometry promotes an efficient exchange between perfusion fluid and brain tissue.

In an embodiment, the clearance between the healing dummy and the flexible tubing is formed by a spacing between an inner surface of the flexible tubing and an outer surface of the healing dummy in a range between about 0.01 mm and about 0.5 mm, particularly in a range between about 0.05 mm and about 0.2 mm. It has turned out that the mentioned distances ensure that no tissue ingrowth can occur between healing dummy and flexible tubing and at the same time allow for a sufficiently low frictional insertion and removal procedure of the healing dummy.

In an embodiment, a surface of the healing dummy facing the brain tissue is functionalized. Additionally or alternatively, it is also possible that a surface of the flexible tubing facing the brain tissue is functionalized. Hence, the healing dummy and/or the flexible tubing may be functionalized at a surface thereof facing the brain substance. By a functionalization of that kind, for instance in the form of the surface immobilization of functionalization agents, the desired properties of the catheter may further be promoted.

An antibiotic surface functionalization may inhibit the formation of germs at the implantation site. It is also possible that such a functionalization reduces the surface friction properties of the healing dummy and/or the flexible tubing. More generally, such a functionalization may comprise surface activation, surface deposition, adaptation of surface smoothness, etc. It may suppress fouling, bacterial growth, coagulation, inflammation and/or rejection reactions. It may include surface activation by the introduction of chemical functional groups to a surface. It may also include surface activation, for instance antibacterial, anticoagulational, antiinflammational, antiadhesive surface treatment.

In an embodiment, the healing dummy is made of a fluoropolymer, particularly of polytetrafluorethylene (PTFE). Other suitable materials include perfluoroalkoxy (PFA), fluorinated ethylene propylene (FEP), or ethylene tetrafluoroethylene (ETFE). It has turned out that a fluoropolymer, particularly PTFE, is particularly suitable as material for the healing dummy since this is a low friction bioinert material which allows the insertion into the physiological subject with a low risk of injury. Also the flexible tubing may be made of such a fluoropolymer material.

In an embodiment, the perfusion insert comprises a hollow cylindrical tube delimiting an inner lumen and delimiting together with the flexible tubing an annular outer lumen, wherein the inner lumen is configured for supplying the perfusion fluid to the brain and the annular lumen is configured for collecting the perfusion fluid, or vice versa. Such an embodiment may relate to a microperfusion catheter, for instance an open-flow microperfusion catheter.

In an embodiment, the perfusion insert comprises a multi-lumen structure delimiting in its interior multiple lumen (for instance concentrically arranged annuli and/or lumen arranged side by side), wherein one or more of the multiple lumen is/are configured for supplying the perfusion fluid to the brain and one or more of the multiple lumen is/are configured for collecting the perfusion fluid. Such a structure allows for more sophisticated fluid exchange functions, since various fluid supply and fluid removal procedures may be performed at the same time. For instance, it is possible to supply via a first lumen a perfusion fluid and to supply via a second lumen a medication.

In an embodiment, the perfusion insert comprises a permeable membrane between the catheter on the one hand and tissue surrounding the catheter on the other hand. Such an embodiment may relate to microdialysis. The term "permeable" may in this context particularly denote a material property of a corresponding membrane, namely that the membrane can be traversed—in a significant manner or quantity—by fluidic or solid particles having specific sizes. For instance, such a membrane may be permeable for substances being smaller than a cut-off size of the membrane, but being impermeable for substances being larger than a cut-off size of the membrane.

In an embodiment, the perfusion insert comprises a mesh of a filament structure between the catheter on the one hand and tissue surrounding the catheter on the other hand, wherein filament material of the filament structure is impermeable and gaps between adjacent portions of the filament material are permeable. Hence, a catheter structure is provided having an exchange surface made of a filament structure. Thus, wound filaments or filament portions may be cross-linked or interconnected or attached/aligned to one another in such a manner that macroscopic and/or microscopic holes are formed between the network of filament portions serving as permeable regions, whereas the solid structure of the filaments may be impermeable. Thus, by adjusting the cross-linking properties or alignment properties of the filament portions, it may be possible to flexibly adjust the size of the openings, thereby allowing to properly design the material exchange properties of the exchange surface of the catheter. Thus, such a catheter does not have to include a porous material, i.e. an essentially two-dimensional impermeable substrate in which a plurality of pores are formed, but in contrast to this an interwoven structure of essentially one-dimensional filaments may define the material exchange properties.

In an embodiment, the flexible tubing has a wall thickness in a range between about 0.01 mm and about 0.3 mm, particularly in a range between about 0.02 mm and about 0.15 mm. These ranges are highly advantageous, particularly when the tubing is made of a flexible plastic material, in order to allow at the same time a simple insertion of the flexible tubing into a bore in the cranium and from there towards the brain but also being sufficiently flexible so as to prevent surrounding brain tissue from severe injuries. For the reason of a simple insertion, the thickness of the flexible tubing may be not too small, and for the purpose of injury prevention, the thickness may not be too large to provide sufficient flexibility.

In an embodiment, the flexible tubing is made of a material which has a Shore hardness in a range between about D30 and about D90, particularly in a range between about D50 and about D70. Thus, the given hardness values relate to a Shore hardness test. This test measures the resistance of a plastic towards indentation and provides an empirical hardness value. Shore hardness using the Shore D scale is a preferred method for rubbers/elastomers and is also commonly used for even softer plastics such as polyolefins, fluoropolymers, and vinyls. The Shore hardness is measured with an apparatus known as a Durometer and consequently is also known as "Durometer hardness". The hardness value is determined by the penetration of a Durometer indenter foot into the sample. The given values may relate to methods of ISO 7619-1:2010, ISO 868, in the latest version available at the priority date of this patent application.

In an embodiment, the catheter is configured for microdialysis or for microperfusion, particularly for open-flow microperfusion (OFM). The term "microdialysis" may particularly denote a method which is mainly based on diffusion through a permeable membrane. It may be used for monitoring analyte concentrations, wherein two phases are separated by a (semi-)permeable membrane. A first phase may be a milieu to be investigated by monitoring the concentration of one or several analytes. A second phase may be a liquid phase into which analytes diffuse and equilibrate partially or fully with the first phase, without systemically altering the concentration of the analyte in the first phase. The term "microperfusion" may particularly denote a system of monitoring analyte concentrations, wherein in contrast to microdialysis no membrane is used but an exchange occurs via a small open gap between two adjacent structures.

In an embodiment, the surface roughness (in terms of RMS roughness) of the flexible tube and/or of the healing dummy, as measured by Atomic Force Microscopy (AFM), may be in a range between about 1 nm and about 100 nm, particularly in a range between about 1 nm and about 50 nm, more particularly in a range between about 3 nm and about 20 nm. With such smooth surfaces, the risk of injuries may be kept at a very low level, and the growth of tissue on such a smooth substrate is also very small.

In the following, further exemplary embodiments of the medical system will be explained. However, these embodiments also apply to the catheter and the method.

In an embodiment, the medical system comprises a sensor unit being supplyable with the sample fluid by the pump and being configured for sensing a value of a physiological parameter by analyzing the sample fluid. The term "physiological parameter" may particularly denote any parameter which is related to the physiology of an organism, for instance the metabolism, etc. Such a physiological parameter may include the concentration of a hormone, a protein concentration, etc. Particularly, the physiological parameter may denote a glucose concentration. Hence, when a sensor unit is provided as a part of the medical system, online sensing is possible, i.e. sensing during the fluid processing. For example, the sensing of a physiological parameter may be performed by analyzing the sample fluid, for example by mixing it with an enzyme to generate a detectable product. The result of the analysis may be displayed in real time on a display device of the medical system. One application of embodiments of the invention is the screening of pharmaceutical substances.

In an embodiment, the sensor unit is configured for continuously monitoring a physiological parameter by analyzing the sample fluid, particularly is configured for glucose monitoring. Since glucose can pass the blood-brain barrier, it can also be detected in the brain tissue. By continuously measuring the value of the physiological parameter, it is possible to monitor the parameter. Particularly for diabetes patients, it is possible to continuously monitor the glucose level so as to trigger an alarm in case of a too large or too high glucose level.

In an embodiment, it is optionally possible to supply a physiologically active substance, for instance via the perfusion fluid, in order to bring the physiological parameter to a desired value. The term "physiologically active substance" may particularly denote any substance which may have an effect on the physiology of the living organism, for instance a medication, a drug, etc.

In an embodiment, the medical system comprises a sample fluid collection container configured for collecting the sample fluid for subsequent offline analysis. After exchange with brain tissue of the patient, the resulting sample fluid can be pumped to a sample container which may be disassembled from the medical device for later offline analysis.

In an embodiment, the pump (for instance a syringe pump) is configured for conducting the perfusion fluid towards the catheter with basically the same flow rate according to which the sample fluid is conducted away from the catheter, for instance towards a sensor or a collection container. This may ensure maintenance of an equilibrium between supplied fluid and sucked fluid to prevent any undesired physiological influence (such as oedema) which may result from an unbalanced supply and drain of fluid.

In an embodiment, the medical system comprises a blood-brain barrier integrity detector configured for detecting, after having substituted the healing dummy by the perfusion insert, whether the blood-brain barrier has recovered after potential injury caused by the implantation of the healing dummy. Thus, it can be ensured by such a test that the actual subsequent monitoring of the physiological parameter and/or supply of a medication is performed under intact physiological conditions and not in a disturbed state of the blood-brain barrier which may cause measurement artefacts.

In an embodiment, the blood-brain barrier integrity detector is configured for detecting whether the blood-brain barrier has recovered by detecting whether a marker substance (which is not transferable from the blood to the brain in case of an intact blood-brain barrier, but which may be transferable from the blood to the brain in case when the blood-brain barrier is disturbed) supplied to blood of the physiological subject by a marker supply unit is detectable in the perfusion fluid. In other words, for testing blood-brain barrier integrity, a marker substance may be injected into the blood of the physiological subject by a marker substance catheter or syringe of the medical system in order to check whether this marker can pass the barrier between blood system and brain system. If this is the case, the marker can be detected by the blood-brain barrier integrity detector showing that the injury has not yet sufficiently healed so that the healing dummy needs to be inserted again and it is necessary to wait a further time interval until the actual monitoring procedure can be initiated. If however no such a marker substance can be measured by the blood-brain barrier integrity detector, it can be concluded that the blood-brain barrier integrity is already recovered and that the actual measurement mode can be started.

In an embodiment, the perfusion fluid comprises a mixture of NaCl and/or MgCl and/or $CaCl_2$ and/or KCl and/or $NaH_2PO_4$ and/or $Na_2HPO_4$ and/or glucose. The perfusion fluid may be a dedicated brain perfusion fluid, i.e. a mixture of components known by the skilled person to be appropriate for perfusion in the brain.

In an embodiment, the perfusion fluid comprises a mixture of about 130±10 mmol/l Na, about 4.3±0.5 mmol/l K, about 0.72±0.10 mmol/l Ca, about 0.40±0.08 mmol/l Mg, about 135±10 mmol/l Cl, and about 3±1 mmol/l glucose. One or more of these components may be omitted. For perfusing the brain of a physiological subject such as a human being, the given mixture of substances is advantageous. For example, the perfusion fluid may be configured as disclosed by McNay E. C., Sherwin, R. S., "Journal of Neuroscience Methods", 132, 2004, pages 35-43. However, some deviations from the given values/ranges are possible.

In an embodiment, the perfusion fluid comprises a medication. With such a system, it is possible to supply a physiologically active substance into the brain and to measure the response of the physiological subject to the supply of this active pharmaceutical ingredient. For example, in such an embodiment, it is possible to perform pharmascreening.

For generating an access bore to the brain, it is possible to bore a hole in the cranium and to also cut a hole in the dura mater.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 1, FIG. 2, FIG. 3 and FIG. 4 show different states during implanting a cerebral catheter according to an exemplary embodiment of the invention to a brain of a human being.

FIG. 5 shows a medical system according to an exemplary embodiment of the invention comprising the cerebral catheter implanted according to FIG. 1 to FIG. 4 in a perfusion mode.

FIG. 6 shows a healing dummy inserted into a flexible tubing of a catheter according to an exemplary embodiment of the invention.

FIG. 7, FIG. 8 and FIG. 9 show three different examples of a perfusion insert according to exemplary embodiments of the invention inserted into the flexible tubing of FIG. 6 substituting the healing dummy.

FIG. 10 shows the geometrical conditions between the flexible tube and a healing dummy/a perfusion insert of a cerebral catheter according to an exemplary embodiment of the invention.

FIG. 11 and FIG. 12 show tables indicative of a composition of a perfusion fluid particularly appropriate for brain catheters.

DETAILED DESCRIPTION OF EXEMPLARY EMBODIMENTS

Figure 13:
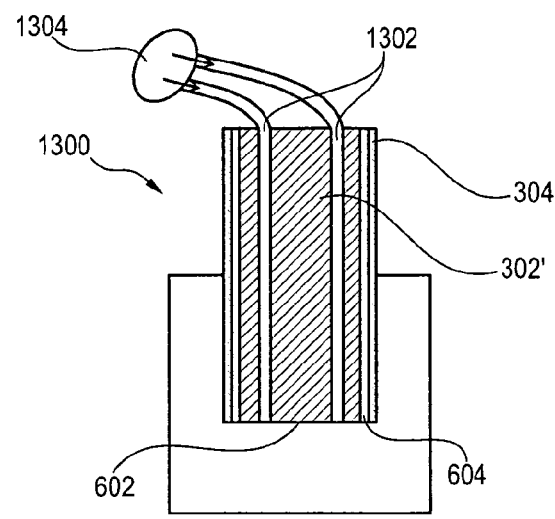
FIG. 13 shows a healing dummy having a venting unit and being inserted into a flexible tubing of a catheter according to an exemplary embodiment of the invention.

The illustration in the drawing is schematically. In different drawings, similar or identical elements are provided with the same reference signs.

FIG. 1 shows a cross-sectional simplifying view of a brain of a human being, wherein for purposes of a schematic illustration only some of the anatomic components are mentioned. FIG. 1 shows a cranial bone 100 covering the different layers of the meninges 102. The actual cerebrum or brain is denoted with reference numeral 104. Between the meninges 102 and the brain 104, a space 106 with brain fluid (or cerebral fluid) as well as blood vessels is interposed.

As can be taken from FIG. 2, a bore 200 is formed traversing components 100 and 102 for subsequent implantation of a cerebral catheter according to an exemplary embodiment of the invention.

As can be taken from FIG. 3, a part of a cerebral catheter 300 according to an exemplary embodiment is then inserted into the bore 200 (for sampling extracellular brain fluid, components 300, 302, 304, 306, 308 will extend up to the brain 104). In one embodiment, a healing dummy 302 arranged in a lumen of a flexible tubing 304 is inserted together into the bore 200. In another embodiment, it is possible that first the flexible tubing 304 is inserted into the bore 200, and subsequently the healing dummy 302 is inserted into a central lumen of the flexible tubing 304. Hence, the flexible tubing 304 has an inner lumen (denoted with reference numeral 400 in FIG. 4) and forms an outer boundary between the catheter 300 and surrounding brain tissue when the catheter 300 is implanted. The healing dummy 302 is inserted in the lumen of the flexible tubing 304 with some clearance (in other words, there is a small gap between an exterior surface of the healing dummy 302 and an interior surface of the flexible tubing 304) so as to prevent tissue ingrowth from the brain 104 into the lumen as long as the healing dummy 302 remains located within the lumen. As can be taken from FIG. 3 as well, the healing dummy 302 has an edgeless rounded surface 306 facing the brain tissue (i.e. reference numerals 106, 104) when being inserted in the flexible tubing 304. The flexible tubing 304 is a PTFE (Teflon®) tube having a wall thickness of 0.05 mm and having a Shore hardness with a value D60. Furthermore, the roughness of an exterior surface of the flexible tubing 304 is 8 nm. Also the healing dummy 302 is made, in the present embodiment, of PTFE and has a surface roughness at the rounded surface 306 of about 8 nm. A small annular gap 308 having a width of 0.1 mm is formed between the flexible tubing 304 and the healing dummy 302 so that it is basically prevented that any solid tissue of brain grows into the annular gap between the flexible tubing 304 and the healing dummy 302. The healing dummy 302 is shaped as a circular cylinder with a rounded front face, and the flexible tubing 304 is shaped as a hollow circular cylinder. As can further be taken from FIG. 3, when the healing dummy 302 is inserted in the flexible tubing 304, it protrudes over an end of the flexible tubing 304 by a small distance of, in the present embodiment, 0.1 mm.

During the implantation procedure of FIG. 2 and FIG. 3, it can happen that the brain is slightly injured which may also have the effect that the blood-brain barrier is temporarily deactivated. In order to postpone the start of the monitoring of a physiological parameter such as the glucose level until the injury has been healed and the blood-brain barrier is again intact, the healing dummy 302 stays within the flexible tubing 304 for a certain time of for instance 20 days. From medical experience, it is known that 20 days are in many cases sufficient so that the blood-brain barrier is recovered. After expiry of a corresponding time period, the healing dummy 302 can be removed from the flexible tubing 304 by simply retracting it in an upward direction according to FIG. 3, compare pulling arrow 402. Due to the clearance between the healing dummy 302 and the flexible tubing 304, the removal of the healing dummy 302 can be performed in a frictionless manner (what concerns the sliding between the healing dummy 302 and the flexible tubing 304), i.e. without exerting significant forces to the surrounding tissue. Therefore, it can be safely prevented that a new injury of the brain occurs due to the removal of the healing dummy 302.

Hence, as can be taken from FIG. 4, the flexible tubing 304 alone remains within the brain so that the inner lumen 400 is exposed.

FIG. 5 shows a medical system 500 according to an exemplary embodiment of the invention which includes the catheter 300, now in an operation mode in which a perfusion insert 502 has been inserted into the lumen 400 delimited by the flexible tubing 304, as well as including further components.

The perfusion insert 502 is inserted in the lumen 400 after having removed the healing dummy 302 from the lumen 400, i.e. as a substitution therefore. The perfusion insert 502 is configured, i.e. has a corresponding supply interface 540, for supplying a perfusion fluid from a perfusion fluid container 504 to the brain so as to initiate an interaction between the perfusion fluid and brain tissue. The perfusion insert 502 is further configured, i.e. has a corresponding drain interface 550, so that perfusion fluid can be collected after the interaction with the brain tissue (hence, a sample fluid having contributions of the initial perfusion fluid and of the brain tissue, particularly brain fluid thereof). In the embodiment of FIG. 5, the perfusion insert 502 forms, together with the flexible tubing 304 and the connected pump configuration which will be described below in more detail, an open flow microperfusion catheter.

The medical system 500 furthermore comprises a pump 506 which is in fluid communication with the catheter 300 and conducts the perfusion fluid from the perfusion fluid container 504 to the inner lumen 400 within the perfusion insert 502. The perfusion fluid then mixes with brain fluid or other kind of brain tissue, and after this interaction, the corresponding sample fluid is pumped back via an annular space 508 via the pump 506 away from the catheter 300.

A control unit 510 (such as a microprocessor or a central processing unit) controls operation of the various components of the medical system 500. Particularly, the pump 506 is controlled by the control unit 510. Furthermore, the control unit 510 controls a valve 512 which can be opened or closed so as to pump the perfusion fluid with a predetermined flow rate towards the catheter 300. The control unit 510 furthermore controls a valve 514 which connects the sample fluid with a sensor 516. The sensor 516 is supplyable with the sample fluid by the pump 506 and senses a value of a physiological parameter such as the glucose level by analyzing the sample fluid. Hence, an online sensing method is implemented in the medical system 500. Also the sensor 516 is controlled by the control unit 510 and may report the result of the sensing to the control unit 510. Alternative sensing is possible, for instance brain pressure measurement.

Optionally, it is possible to verify with medical system 500 whether the blood-brain barrier is in fact again intact after the healing procedure, as will be described in the following in more detail. A marker substance (for instance evans blue and sodium fluorscein) may be supplied to the blood of the patient (not shown). The marker substance is selected so that it cannot pass an intact blood-brain barrier. If the blood-brain barrier is still disturbed by the implantation injury, the marker may pass the blood-brain barrier and may be sucked by the pump 506 via a valve 522 controllable by the control unit 510 towards a marker detection unit 524. The marker detection unit 524 determines whether the marker can be detected and provides a corresponding result to the control unit 510. If the marker is identified in the brain tissue by the marker detection unit 524, it is possible to reinsert the healing dummy 302 into the lumen 400 so as to continue the healing procedure without the danger of tissue ingrowth. If however no markers are detected by the marker detection unit 524, the supply of a perfusate fluid as described above can be initiated.

As one of many alternatives to the embodiment of FIG. 5, it is possible to substitute the peristaltic pump 506 by syringe pumps. Such syringe pumps may be included in containers 516, 524, 526, 504. In such an embodiment, the valves 522, 514, 512, 528 may be omitted. Controller 510 may be directly connected to the syringe pumps.

The above description refers to the supply of a perfusion fluid towards the lumen 400 and the detection of a corresponding sample fluid, for instance for continuous monitoring of the glucose level or any other physiological parameters. However, additionally or alternatively, it is also possible to supply a medication to the brain. For this purpose, a medication container 526 can be provided in which a corresponding medication is stored. Under control of the control unit 510, a valve 528 can be opened so as to supply medication from the medication container 526 to the lumen 400. Alternatively, it is also possible that a medication is within the perfusion fluid stored in container 504.

It may be advantageous to ensure, for instance by a corresponding operation of the pump 506, that the flow rate of the supplied fluid is equal to the volume of the fluid recovered from the annulus 508 so as to prevent the formation of oedemas and other undesired physiological conditions in the brain.

During the implantation, the healing dummy 302 is located in an interior of the outer flexible tubing 304 of the catheter 300. The healing dummy 302 remains within the flexible tubing 304 until the implantation trauma is healed. The healing dummy 302 effectively prevents growth of tissue into an interior of the flexible tubing 304. Before carrying out the actual measurement or monitoring of the physiological parameter, the healing dummy 302 is removed and the inner tubing 502 is inserted into the outer tubing 304 forming a larger annular volume (see reference numeral 508) as compared to the scenario in which the healing dummy 302 is inserted into the flexible tubing 304. The dimensions and the position of the inner tubing 502 and the healing dummy 302 are configured so that no new additional irritation of the tissue occurs. Also a pressureless removal of the healing dummy 302 by means of a ventilation unit (not shown) may reduce the risk of new additional irritation of the tissue. During the actual measurement, the perfusion fluid is conducted as a measurement fluid through the inner tube 502 into the tissue. With the same pump speed fluid is withdrawn via the annulus 508 between the outer tubing 304 and the inner tubing 502 so that the liquid volume remaining in the tissue is zero or very close to zero. After the measurement, it is possible to again substitute the inner tubing 502 by the healing dummy 302. The measurement can be repeated as often as desired without a new damage of the tissue.

In FIG. 3 to FIG. 5, the front face of the outer tubing 304 and healing dummy 302 arrangement as well as the front face of the outer tubing 304 and inner tubing 502 arrangement are aligned with a surface of brain 104. However, these arrangements may alternatively be forwarded or advanced further into the brain 104. The surface of the brain in such an embodiment is indicated by dashed lines 320 in FIG. 3 to FIG. 5, so that the catheter 300 then penetrated into the brain 104.

FIG. 6 shows a catheter 600 according to another exemplary embodiment in an operation mode in which a cylindrical healing dummy 302 has been inserted into an interior lumen of the cylindrical flexible tube 304. In contrast to the embodiment of FIG. 3, the front surface 602 of the healing dummy 302 facing the tissue is planar so that, in combination with the high flexibility of the flexible tubing 304, the arrangement 600 is not prone to cause a new injury. As can again be taken from FIG. 6, the gap 604 is sufficiently small so as to prevent tissue ingrowth from the brain into the catheter 600.

After having removed the healing dummy 302 from catheter 600, it is possible to insert one of the perfusion inserts shown in the embodiments of FIG. 7, FIG. 8 and FIG. 9.

The embodiment of FIG. 7 corresponds to the embodiment of FIG. 5 and shows that a dual lumen catheter can be formed by inserting the tubular insert 502 into the lumen 400. This relates to a flow-through catheter architecture in which a mixture of perfusion fluid supplied via the lumen 400 and brain fluid is conducted to the annulus 508, as indicated schematically by reference numeral 700. As can be taken from FIG. 7, the width of the annulus between the tubular insert 502 and the flexible tubing 304 is larger than the width of the annulus between the healing dummy 302 and the flexible tubing 304.

In the alternative embodiment of FIG. 8, a multi-lumen catheter is formed by configuring the perfusion insert from a multi-walled structure 800 so that a plurality of tubular or circular lumen 802 is formed. As can be taken from arrows 804, an even more complex fluid exchange architecture can be realized with the embodiment of FIG. 8.

The embodiment of FIG. 9 does not rely on the principle of microperfusion as the embodiments of FIG. 7 and FIG. 8, but relates to a microdialysis catheter. After having removed the healing dummy 302 from the flexible tubing 304, an arrangement of tube 502 and a permeable membrane 900 is inserted into the lumen 400 Perfusion fluid is supplied to the lumen 400, as indicated schematically with reference numeral 902. Via the permeable membrane 900, an exchange with the surrounding tissue is possible and the corresponding sample fluid is pumped away via the annulus 508, as indicated schematically by reference numeral 904.

Alternatively, the embodiment of FIG. 9 may also be realized with multiple lumen (for instance as in FIG. 8) and/or the membrane 900 may be substituted by a mesh of filaments.

For an online sensing system, all surfaces of the catheters shown in FIG. 5, FIG. 7 to FIG. 9 can be used for attaching miniaturized wall-integrated sensors, or alternatively sensors arranged as coatings on such surfaces being in contact with sample fluid.

FIG. 10 shows an enlarged view of a part of a catheter 1000 according to an exemplary embodiment of the invention. The wall thickness of the flexible tubing 304, denoted with "s" in FIG. 10, can be in a range between 0.02 mm and 0.15 mm. The Shore hardness of the flexible tubing 304 can be in a range between D50 and D70 mm. A protrusion of the inner tubing 502 over the flexible tubing 304, denoted with "L" in FIG. 10, can be in a range between 0 and 0.5 mm. A distance between the flexible tubing 304 and the healing dummy 302, denoted with "d" in FIG. 10, can be in a range between 0.05 mm and 0.2 mm. A distance "D" between the inner tube 502 and the flexible tubing 304 can be in a range between 0.15 and 0.6 mm, wherein D>d.

FIG. 11 shows a composition of a perfusion fluid to be used as a measurement fluid particularly for cerebral catheters according to exemplary embodiments of the invention.

FIG. 12 shows a table illustrating a possible perfusion fluid with tolerances.

FIG. 13 shows an arrangement 1300 of a healing dummy 302' having a venting unit 1302 and being inserted into a flexible tubing 304 of a catheter according to an exemplary embodiment of the invention. The venting unit 1302 is realized as two through holes extending through the healing dummy 302'. Thus, upon pulling the healing dummy 302' relative to the tubing 304 out of the lumen, it can be prevented that a negative pressure is formed at an interface between the healing dummy 302' and adjacent tissue since a gas can pass through the through holes for pressure equilibration. Avoiding such a negative pressure may prevent anew injury of the tissue upon removing the healing dummy 302'. The number of through holes can vary, and can for instance be one, three, or more.

FIG. 13 shows an additional optional component of the venting unit 1302, i.e. a pump 1304. This pump 1304 may pump a fluid (such as a gas or a liquid) through the through holes while the healing dummy 302' is removed from the tubing 304 so as to actively avoid an underpressure at the interface between the healing dummy 302' and adjacent tissue.

Figure 14:
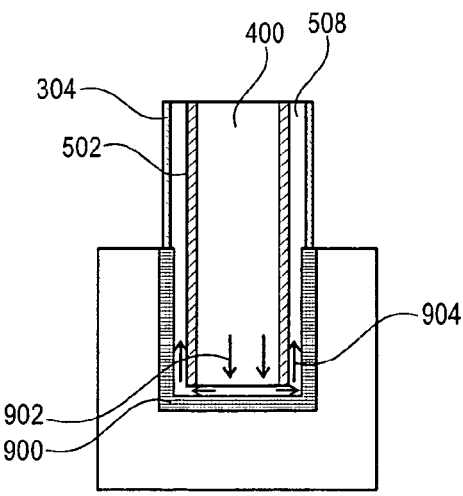
FIG. 14 shows a perfusion insert according to another exemplary embodiments of the invention inserted into the flexible tubing of FIG. 13 substituting the healing dummy.

The embodiment of FIG. 14 is very similar to the embodiment of FIG. 9 to which explicit reference is made for details. However, in contrast to FIG. 9, FIG. 14 implements membrane 900 to enclose also a part of the sidewall. The membrane 900 can be inserted so that the healing dummy 302' (or healing dummy 302) serves for shaping the membrane 900. The membrane 900 can be stretched over the healing dummy during implantation.

Figure 15:
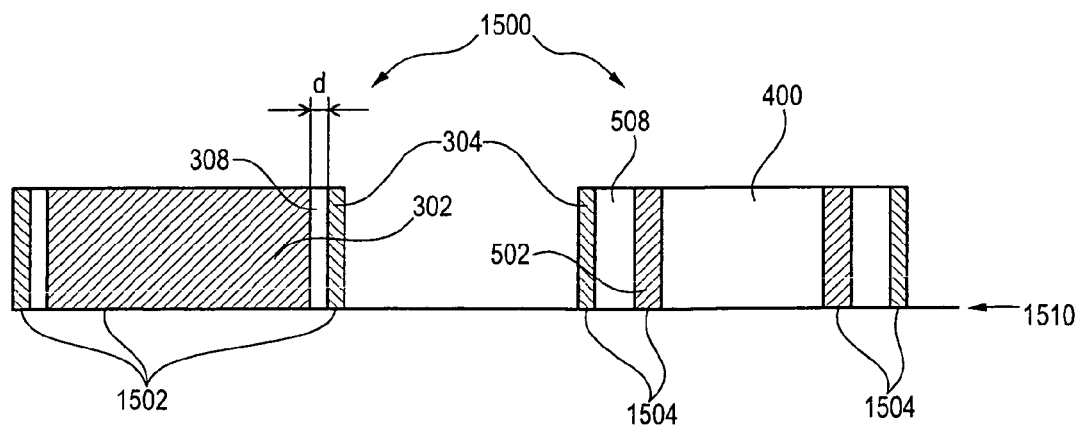
FIG. 15 shows two operation modes of a catheter according to an exemplary embodiment of the invention, wherein one operation mode shows a healing dummy inserted into and flushing with a tubing and the other operation mode shows a perfusion insert inserted into and flushing with a tubing.

FIG. 15 shows two operation modes of a catheter 1500 according to an exemplary embodiment of the invention. One operation mode (on the left hand side) shows a healing dummy 302 inserted into and flushing with a tubing 304. The other operation mode (on the right hand side) shows a perfusion insert 502 inserted into and flushing with the tubing 304. This means that a common flat and planar front surface 1502 of the flushing healing dummy 302 and tubing 304 in the first operation mode equals to or flushes with a common front surface 1504 of flushing perfusion insert 502 and tubing 304. A common flushing line 1510 indicates a common end position up to which the healing dummy 302 and tubing 304 arrangement on the left hand side of FIG. 15 as well as the perfusion insert 502 and tubing 304 arrangement on the right hand side of FIG. 15 extend when being implanted in a physiological environment such as a brain.

Thus, the catheter 1500 is configured so that, when the healing dummy 302 is inserted in the lumen of tubing 304 to prevent tissue ingrowth, the healing dummy 302 and the tubing 304 are in flush (i.e. the healing dummy 302 is inserted in the tubing 304 without protruding over the tubing 304), so that the healing dummy 302 and the tubing 304 together form the flat and planar structure at the common front face 1502. This flushing between front face of healing dummy 302 and front face of tubing 304 is highly advantageous because this fully avoids anew injury of tissue after primary implantation of the catheter 1500. Moreover, also the perfusion insert 502 and the tubing 304 are also in flush and are configured so that, when the perfusion insert 502 is inserted in the lumen of tubing 304, the front surface of the perfusion insert 502 and the front surface of the tubing 304 are aligned to one another. By providing both the healing dummy 302 and the tubing 304 as well as the perfusion insert 502 and the tubing 304 to flush thereby forming an aligned front face being free or basically free of a protrusion, an anew injury of the tissue due to the maneuvering of healing dummy 302 or perfusion insert 502 may be safely avoided after the initial implantation of the catheter 1500.

The aligned or flushing position (as well as the slight protruding position in other embodiments such as in FIG. 10) may be, in an embodiment, defined by cooperating engagement structures (which may form a mechanical locking mechanism) between tubing 304 and healing dummy 302 and/or between tubing 304 and perfusion insert 502. Hence, when advancing healing dummy 302 or perfusion insert 502 into the tubing 304, the cooperating engagement structures may come into engagement to thereby prevent further advancing of healing dummy 302 or perfusion insert 502 into the tubing 304 when the flushing position (or a defined slightly protruding position) is reached. This may simplify operation by a user because the user will experience a mechanical blocking when the desired end position is reached.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:
1. A catheter for implantation into tissue, the catheter comprising:
   a tubing having a lumen and defining at least partially an outer boundary between the catheter and the tissue when the catheter is implanted in the tissue;
   a healing dummy being insertable in the lumen with clearance so as to prevent tissue ingrowth from the tissue into the lumen when the healing dummy is within the lumen, wherein the healing dummy is removable from the lumen by pulling the healing dummy relative to the tubing out of the lumen; and a perfusion insert being insertable in the lumen when the healing dummy is removed from the lumen, being configured for supplying a perfusion fluid to the tissue so as to initiate interaction between the perfusion fluid and the tissue, and being configured for collecting perfusion fluid after interaction with the tissue;

wherein the healing dummy and the tubing are in flush, or the healing dummy protrudes along an insertion direction over the tubing by a distance in a range between 0 and 0.5 mm, wherein the perfusion insert comprises a hollow cylindrical tube delimiting an inner lumen and delimiting together with the tubing an annular lumen, wherein the inner lumen is configured for supplying the perfusion fluid to the tissue and the annular lumen is configured for collecting the perfusion fluid.

2. The catheter of claim 1, wherein the perfusion insert and the tubing are in flush, or the perfusion insert protrudes along an insertion direction over the tubing by a distance in a range between 0 and 0.5 mm.

3. The catheter of claim 1 wherein the healing dummy comprises a venting unit configured for venting a region between the healing dummy and the tissue upon pulling the healing dummy relative to the tubing out of the lumen.

4. The catheter of claim 1, wherein the healing dummy has an edgeless surface facing tissue when being inserted in the tubing.

5. The catheter of claim 1, wherein the healing dummy is configured to completely fill the opening in the tubing so that no recess remains in the tubing when the healing dummy is inserted into the tubing.

6. The catheter of claim 1, wherein the perfusion insert is configured to fill the opening in the tubing apart from one or more fluid channels.

7. The catheter of claim 1, wherein a surface roughness of the tubing and/or of the healing dummy is in a range between 1 nm and 100 nm.

8. The catheter of claim 1, wherein the clearance between the healing dummy and the tubing is formed by a spacing between an inner surface of the tubing and an outer surface of the healing dummy, the spacing being in a range between 0.01 mm and 0.5 mm.

9. The catheter of claim 1, wherein a surface of the healing dummy is functionalized.

10. The catheter of claim 1, wherein the healing dummy is made of a fluoropolymer.

11. The catheter of claim 1, wherein the perfusion insert comprises a multi-lumen structure delimiting in its interior multiple lumen, wherein one or more of the multiple lumen is/are configured for supplying the perfusion fluid to the tissue and one or more of the multiple lumen is/are configured for collecting the perfusion fluid.

12. The catheter of claim 1, wherein the tubing has a wall thickness in a range between 0.01 mm and 0.3 mm.

13. The catheter of claim 1, wherein the tubing is made of a material which has a Shore hardness in a range between D30 and D90.

14. A medical system, comprising:
a catheter including:
a tubing having a lumen and defining at least partially an outer boundary between the catheter and a tissue when the catheter is implanted in the tissue;
a healing dummy being insertable in the lumen with clearance so as to prevent tissue ingrowth from the tissue into the lumen when the healing dummy is within the lumen, wherein the healing dummy is removable from the lumen by pulling the healing dummy relative to the tubing out of the lumen; and
a perfusion insert being insertable in the lumen when the healing dummy is removed from the lumen, being configured for supplying a perfusion fluid to the tissue so as to initiate interaction between the perfusion fluid and the tissue, and being configured for collecting perfusion fluid after interaction with the tissue;
wherein the healing dummy protrudes along an insertion direction over the tubing by a distance in a range between 0 and 0.5 mm, the catheter configured to be inserted into the tissue; and
a pump being in fluid communication with the catheter for conducting the perfusion fluid towards the catheter and for conducting a sample fluid resulting from an interaction of the perfusion fluid with the tissue away from the catheter,
wherein the perfusion insert comprises a hollow cylindrical tube delimiting an inner lumen and delimiting together with the tubing an annular lumen, wherein the inner lumen is configured for supplying the perfusion fluid to the tissue and the annular lumen is configured for collecting the perfusion fluid.

15. The medical system of claim 14, wherein the catheter is a cerebral catheter for implantation into a brain, wherein the medical system comprises a blood-brain barrier integrity detector configured for detecting, after having substituted the healing dummy by the perfusion insert, whether the blood-brain barrier has recovered after an injury by an implantation of the healing dummy.

16. The medical system of claim 14, wherein the blood-brain barrier integrity detector is configured for detecting whether a blood-brain barrier has recovered by detecting whether a marker substance supplied to blood of a physiological subject by a marker supply unit is detectable in the perfusion fluid.

17. The medical system of claim 14, further comprising a perfusion fluid, wherein the perfusion fluid comprises a mixture of NaCl, MgCl, $CaCl_2$, KCl, $NaH_2PO_4$, $Na_2HPO_4$, or glucose.

18. The medical system of claim 14, further comprising a perfusion fluid, wherein the perfusion fluid comprises a mixture of 130±10 mmol/l Na, 4.3±0.5 mmol/l K, 0.72±0.10 mmol/l Ca, 0.40±0.08 mmol/l Mg, 135±10 mmol/l Cl, and 3±1 mmol/l glucose.

19. A method of implanting a catheter into tissue, the method comprising:
implanting the catheter into the tissue so that a tubing having a lumen defines at least partially an outer boundary between the catheter and the tissue;
inserting a healing dummy in the lumen with clearance so as to prevent tissue ingrowth from the tissue into the lumen when the healing dummy is within the lumen and maintaining the healing dummy in the lumen for a predefined healing time;
after expiry of the healing time, removing the healing dummy from the lumen by pulling the healing dummy relative to the tubing out of the lumen;
after the removing, inserting a perfusion insert in the lumen for supplying a perfusion fluid to the tissue so as to initiate interaction between the perfusion fluid and the tissue; and
collecting perfusion fluid after the interaction with the tissue;

wherein the healing dummy and the tubing are in flush, or the healing dummy protrudes along an insertion direction over the tubing by a distance in a range between 0 and 0.5 mm, wherein the perfusion insert comprises a hollow cylindrical tube delimiting an inner lumen and delimiting together with the tubing an annular lumen, wherein the inner lumen is configured for supplying the perfusion fluid to the tissue and the annular lumen is configured for collecting the perfusion fluid.

* * * * *